(12) United States Patent
Tooren et al.

(10) Patent No.: US 11,160,900 B2
(45) Date of Patent: Nov. 2, 2021

(54) TISSUE-ADHESIVE SEALANT DEVICE

(71) Applicant: Polyganics IP B.V., Groningen (NL)

(72) Inventors: Martin Franke Tooren, Bedum (NL); Justin Van Der Veen, Marum (NL); Dirk Erik Muller, Assen (NL); Don Theo Hertsig, Zwolle (NL); Harmen Hendrikus de Vries, Eastermar (NL); Romke Stephan Rudolf Ribbels, Hoogezand (NL)

(73) Assignee: Polyganics IP B.V., Groningen (NL)

( * ) Notice: Subject to any disclaimer, the term of this patent is extended or adjusted under 35 U.S.C. 154(b) by 0 days.

(21) Appl. No.: 16/651,475

(22) PCT Filed: Oct. 1, 2018

(86) PCT No.: PCT/NL2018/050649
§ 371 (c)(1),
(2) Date: Mar. 27, 2020

(87) PCT Pub. No.: WO2019/066657
PCT Pub. Date: Apr. 4, 2019

(65) Prior Publication Data
US 2020/0261615 A1     Aug. 20, 2020

(30) Foreign Application Priority Data

Sep. 29, 2017   (NL) .................................... 2019652

(51) Int. Cl.
| | | |
|---|---|---|
| *A61L 24/04* | (2006.01) |
| *A61L 24/00* | (2006.01) |
| *C08L 67/04* | (2006.01) |
| *C08L 69/00* | (2006.01) |
| *C08L 75/04* | (2006.01) |

(52) U.S. Cl.
CPC ......... *A61L 24/043* (2013.01); *A61L 24/0036* (2013.01); *A61L 24/0042* (2013.01); *C08L 67/04* (2013.01); *C08L 69/00* (2013.01); *C08L 75/04* (2013.01)

(58) Field of Classification Search
CPC ............... A61L 24/043; A61L 24/0036; A61L 24/0042; C08L 67/04; C08L 69/00; C08L 75/04
See application file for complete search history.

(56) References Cited

U.S. PATENT DOCUMENTS

| 8,460,378 B2 * | 6/2013 | Gogolewski | A61L 27/58 623/11.11 |
| 2011/0123476 A1 * | 5/2011 | Kapiamba | A61L 24/04 424/78.06 |

FOREIGN PATENT DOCUMENTS

| CN | 102002142 | * | 7/2012 |
| EP | 1308473 | * | 5/2007 |
| WO | 99/64491 A1 | | 12/1999 |
| WO | WO 9964491 | * | 12/1999 |
| WO | 2008005207 A2 | | 1/2008 |
| WO | 2011079336 A1 | | 7/2011 |
| WO | 2012052527 A1 | | 4/2012 |
| WO | 2016108242 A1 | | 7/2016 |

* cited by examiner

*Primary Examiner* — Shirley V Gembeh
(74) *Attorney, Agent, or Firm* — Banner & Witcoff, Ltd.

(57) ABSTRACT

The invention is directed to a biodegradable tissue-adhesive device for sealing tissue, said device comprising a tissue-adhesive layer which comprises a blend of a tissue-reactive polymer and a biodegradable carrier polyurethane according to the formula of $A-B-C-B_n$, wherein A denotes a polyol, B denotes a diisocyanate moiety, C denotes a diol component and n denotes the number of recurring units, and wherein the B-C-B segment is bioresorbable.

20 Claims, 5 Drawing Sheets

TISSUE-ADHESIVE SEALANT DEVICE

RELATED APPLICATIONS

This application is a National Stage Application under 35 U.S.C. 371 of co-pending PCT application PCT/NL2018/050649 designating the United States and filed Oct. 1, 2018; which claims the benefit of NL application number 2019652 and filed Sep. 29, 2017 each of which are hereby incorporated by reference in their entireties.

The invention is in the field of bioresorbable adhesive materials for medical applications. In particular, the invention is directed to a tissue-adhesive polymer blend and devices comprising such a blend, which are used for sealing tissue, in particular tissue inside the human or animal body such as in the ventral cavity (including the abdominal, thoracic and pelvic cavities) like liver, lung, pancreas, spleen, bladder, kidney and/or intestine tissues.

Tissue-adhesive materials are used in a variety of medical applications. These materials are for instance used to cover or seal wounds to prevent or reduce leakage of bodily fluids. A particular application for tissue-adhesive materials is the sealing of tissue inside the human or animal body. For instance, after trauma or surgery, opened or damaged tissue needs to be sealed to prevent further complications and/or to stimulate the healing process. For this purpose, non-bioresorbable solutions have been provided, but these solutions suffer from the drawback that post-surgical removal of the devices is required.

An example of a bioresorbable device is described in WO2011/079336. Herein a hemostatic sponge, available under the tradename Hemopatch™, is described that is based on a blend of biological polymers such as collagen, gelatin, fibrin or polysaccharides blended with a tissue-adhesive polymer such 4-armed polyethylene glycol that is functionalized with glutarate ester spacer functionalized with N-hydroxysuccinimide. A drawback of the device described herein and available as Hemopatch™ is that it detaches from the tissue already after a few minutes and can therefore only be used for its intended use; the control of bleeding.

Another frequently used product which is used as a tissue sealant is available under the tradename Tachosil™ (Takeda), which is based on fibrin of both human and animal origin. Fibrin based glues are difficult to manufacture and use human and/or animal blood as a fibrin source, entailing the potential risk of transferring diseases and eliciting undesired and fatal immune responses. Moreover, fibrin-based sealants such as Tachosil™ are ineffective in reducing postoperative resection surface related complications such as leakage, bleeding and abscess formation. Therefore, routine use of fibrin sealants is not recommended. Fibrin sealants are not resistant to body fluids such as bile. Detachment of the product from the tissue takes place within minutes. The product is therefore limited to its intended use; the control of bleeding.

Yet another frequently used tissue-sealant device is available from Covidien under the tradename Veriset™. This device consists of three layers, a first later of oxidized cellulose (likely to promote hemostasis), a second middle layer of trilysine and a third layer of 4-arm PEG NHS polymer. A drawback of this device is that it is not resistant to bile and other bodily fluids and it is degraded within 24 hours after application. This device is therefore not suitable for sealing tissue for a longer period.

In WO 2012/052527, a bioresorbable patch comprising an adhesion barrier component layer and a synthetic adhesive polymer component layer is disclosed. A drawback of this construct is the use of polysaccharides in the synthetic adhesive polymer component layer and/or a lack of another supporting polymer in this layer as this generally results in poorer adhesion properties.

It is desirable that the tissue-adhesive materials are resistant to bile and other (acidic) bodily fluids such that the tissue-adhesive materials can be used to prevent or limit intra and post-surgical bleeding and leakage of bodily fluids. For instance, after hepatobiliary and pancreatic surgery, bleeding and loss of other fluid is still a major problem for which improved sealant materials are desired.

It is furthermore desired that the tissue-adhesive material is characterized by a number of properties. The tissue-adhesive bioresorbable material should be biocompatible meaning that it is non-toxic and causes minimal inflammatory and/or immune response. It is further preferred that the tissue-adhesiveness does not have an irritating effect and/or inhibit the healing process of the tissue. This biocompatibility may inter alfa be achieved by a bioresorbable nature of the material. Bioresorbability in this respect means that the material can be broken down by, and be cleared from the body and does not require mechanical removal. The breakdown of the materials typically occurs through hydrolysis and/or enzymatic cleavage into smaller compounds that may be metabolized or excreted, for instance via the kidneys or liver. However, it is typically also preferred that the breakdown of the materials does not occur too rapidly due to bodily fluids such as bile as described above. The time period for healing of a liver tissue is typically in the range of 7 to 14 days. Tachosil®, Veriset® en Hemopatch® are not sufficiently resistant to bile to stop bile leakage. It is desirable that the breakdown of the material thus occurs after 7 days, preferably after 14 days. Resistance to other bodily fluids such as air, intestinal fluids, stomach juice and the like is also preferred such that for instance anastomotic and esophageal perforation leakage may also be treated.

It is further required that the device has a sufficient adhesive strength to tissue. Moreover, it is preferred that the device is applied easily by a surgeon during surgery.

The present invention is directed to a device that addresses at least one of the above-described preferences and drawbacks of known devices.

Accordingly, the present invention is directed to a biodegradable tissue-adhesive device for sealing tissue. Said device comprises a tissue-adhesive layer which comprises a blend of a tissue-reactive polymer and a biodegradable carrier polyurethane according to the formula of ${+}$A-B-C-B${+}_n$, wherein A denotes a polyol, B denotes a diisocyanate moiety, C denotes a diol component and n denotes the number of recurring units, and wherein the B-C-B segment is bioresorbable.

Advantageously, the carrier polyurethane makes it possible to easily vary the structure of the device (i.e. for instance a foam, gel or sheet may be formed). Moreover, the bioresorbability of the carrier polyurethane can be modified by variation of the chemical composition.

The carrier polyurethane is present in the blend to provide structural support to the device that comprises the polymer blend. The carrier polyurethane is a biomedical polyurethane as described in PCT/NL2017/050201, which is incorporated herein as a reference in its entirety.

The present inventors found that the use of the blend of the tissue-reactive polymer and the biodegradable carrier polyurethane, when compared to single-polymer-based adhesive layers such as the single-polymer-based coating in Hemopatch™ as described in WO2011/079336, also surprisingly leads to improved adhesive properties, in particular for a longer period of several days (e.g. 7 or 14 days, or even longer). Another advantage of using the present approach with respect to single-polymer-based coatings, is that not all these coatings may sufficiently adhere to the support layer. By providing a blend of the tissue-reactive polymer and the biodegradable carrier polyurethane in accordance with the present invention, this problem can be solved. The time period for healing of a liver tissue is typically in the range of 7 to 14 days. Tachosil®, Veriset® en Hemopatch® are not sufficiently resistant to bile to stop bile leakage. It is desirable that the breakdown of the material thus occurs after 7 days, preferably after 14 days. Resistance to other bodily fluids such as air, intestinal fluids, stomach juice and the like is also preferred such that for instance anastomotic and esophageal perforation leakage may also be treated.

Surprisingly, another advantage of the blend turned out to be an improved efficiency in the use of the tissue-reactive polymer because the total surface of the foam is generally larger (due to the internal surface) when compared to a (smooth) coating, as is for instance the case in Hemopatch™. By suppressing the device in accordance with the present invention, at least part of the additional (internal) surface area can be brought into contact and reaction with the tissue (by formation of a matrix-like structure in the moist environment), while this is not or much less the case when a smooth, dense coating is used. For this reason, a foam structure is particularly preferred.

It is desirable to provide a carrier polyurethane (PU) with improved solubility and biodegradability characteristics, while maintaining the favorable mechanical properties, such as high resistance to tearing for which the polyurethanes of WO99/64491 are known. It was found that this may be achieved by the polyurethane having the general formula A-B-C-B$_n$, wherein A denoted a polyol, B denotes a diisocyanate moiety, C denotes a diol component and n denotes the number of recurring units, and wherein B-C-B is bioresorbable.

The polyurethane of the present invention as described herein is inherently biodegradable due to its chemical structure. However, in preferred embodiments, the biodegradability may be increased as a result of specific choices for the structure of the polyurethane.

For the sake of clarity and conciseness the composition of the polymers and the segments described herein may be defined by and named after the building blocks or monomers from which the polymers and polymer segments are made, or on which they are based. However, if the polymer or polymers segments can be obtained by using different building blocks or monomers, whilst resulting in the same composition (structure), such polymer or polymers segments are included by the specific definition or name as is used herein as well.

Without wishing to be bound by theory, it is believed that the poor biodegradability of conventional polyurethanes as described in the prior art, may be attributed to the limited solubility of hard 5-block segments with a uniform length on which these conventional polyurethanes are based (e.g. BDI-BDO-BDI-BDO-BDI, wherein BDI denotes 1,4-butane diisocyanate and BDO denotes 1,4-butane diol). It was found that the improved biodegradability of the PU is achieved by improving the solubility of the urethane (B-C-B) segment, which in turn may be achieved by decreasing the crystallinity of the urethane segment.

If has been found that a urethane segment wherein at least one, preferably both of the diisocyanate moieties (B) in B-C-B is of a different length than the diol component (C) results in a urethane segment that is bioresorbable.

With the lengths of the diisocyanate moiety and the diol component is meant the length of the parts of the moiety or component that is present in the backbone of the polyurethane. The length of the diisocyanate moiety (B) can also be expressed as the length between the two isocyanate groups of a diisocyanate compound on which the urethane segment is based. Similarly, the length of the diol component (C) can also be expressed as the length between the two hydroxyl groups of a diol compound on which the urethane segment is based. A practical way to express the length of the diisocyanate moiety and the diol component is by the number of atoms of each moiety and/or component present in the backbone of the urethane segment between the urethane moiety. For instance, a urethane segment based on 1,6-hexane diisocyanate (HDI) and 1,4-butane diol (i.e. B-C-B being HDI-BDO-HDI) thus comprises two diisocyanate moieties having a length of six atoms and a diol component having a length four atoms.

In contrast to polyurethanes comprising a urethane segment with diisocyanate moieties and a diol component having the same length, the hard segment wherein the diisocyanate moiety (B) is of a different length than the diol component (C) has a decreased crystallinity; likely since the urethane moieties in the urethane segments are less well aligned for hydrogen bonding. The limited hydrogen bonding is believed to result in a reduced crystallinity.

It is described in WO99/64491 that the uniformity of the urethane-based urethane segments is the crucial factor for the mechanical properties of the materials. However, it was found that similar mechanical properties can also be obtained by having urethane segments with a multiform length and that this multiformity in fact improves the biodegradability of the biomedical polyurethane.

In a particular embodiment of the present invention, the B-C-B segment (also referred to herein as urethane segment) of the biomedical polyurethane has a multiform block length.

The terms "segment" and "block" as used herein, refer to a polymeric structure of any length. In the art of polymer technology, a long polymeric structure is often referred to as a block, whereas a short polymeric structure is often referred to as a segment. Both these conventional meanings are understood to be comprised in the term "segment" as well as in the term "block" as used herein.

It may be appreciated that, as is common in the field of polymer chemistry, the polyurethane of the present invention may in fact have a certain polymeric weight distribution. When referring herein to the biomedical polyurethane, also a mixture of polyurethanes based on different compounds is meant. This mixture may be the result of different types of polyol (soft) segment and/or of different types of the urethane segment. For instance, the urethane segment may be based on a mixture of different diols (C) and/or diisocyanates (B). Similarly, a single polyurethane polymer molecule may comprise a mixture of B-C-B segments. In fact, the polyurethanes comprising a urethane segment with a multiform block length are typically obtained by having a mixture of different diols (vide infra). Moreover, the diisocyanates B in the polyurethane according to formula (A-B-C-B) may be the same or may be different. Accordingly, a certain single B-C-B segment within the polyurethane may comprise two of the same or two different diisocyanates B. Similarly, the polyurethane may also comprise a mixture of different polyols or a single type of polyol.

In contrast to polyurethanes comprising a urethane segment with a uniform length, the multiform block lengths result in a system wherein the urethane segment has decreased crystallinity, since the urethane moieties in the urethane segments are not well aligned for hydrogen bonding. The limited hydrogen bonding is believed to result in a reduced crystallinity.

The reduced crystallinity, and as such the improved biodegradability, can already be observed by having only a small amount (e.g. 5 mol %) of urethane segments with a diverging length. Preferably, less than 95 mol %, more preferably less than 80 mol %, even more preferably less than 70 mol %, most preferably less than 60 mol % of the B-C-B segments are having the same length.

A particular facile way to express the block length of the urethane segment is by the (theoretical) number of linear atoms comprised in the backbone of the segment excluding the three atoms comprised in each urethane bond (i.e. —O—C(O)—NH—), which can be e.g. determined upon the preparation of the polyurethane. Preferably, the urethane segments comprise on average of more than 12, preferably more than 14, more preferably more than 16 linear atoms in the back bone. The mechanical properties of the materials (e.g. a sheet) based on the polyurethane of the present invention preferably have a modulus of 1-50 MPa. A 3.5 wt % foam prepared by solvent casting has typical a compression of between 2.5 and 10 kPa.

The biodegradability of the urethane segment can also be increased by limiting the number of urethane bonds per (A-B-C-B) unit, which are capable of forming the hydrogen bonds, to four or less. As such, it is preferred that the B-C-B is based on two diisocyanate units. Again, without wishing to be bound by theory, limiting the hydrogen bonding is believed to result in a reduced crystallinity. Since B denotes a diisocyanate block, it is thus preferred that C is not based on a diisocyanate block. As a result, such polyurethane does not comprise a 5-block urethane segment but instead comprises a 3-block urethane segment.

The embodiment wherein B-C-B is based on two diisocyanate units and is of a uniform block length, the biodegradability of the B-C-B segment is generally better than uniform blocks being based on more than two (e.g. three) diisocyanate units (e.g. B-C-B-C-B blocks). As such, in this particular embodiment, the B-C-B segment may be of a uniform block length, however this is not always required and the B-C-B segment may also be of a multiform length and/or a segment wherein the diisocyanate moiety (B) is of a different length than the diol component (C) as described herein above.

As explained herein above, it has been found that the length of the urethane segment influences the mechanical properties of the polyurethane. It has been found that in case the polyurethane comprising a urethane segment that is based on two diisocyanate units, good mechanical properties are obtained if the B-C-B segment comprises more than 12, preferably more than 14, more preferably more than 16 linear carbon atoms in the back bone.

In a preferred embodiment, the B-C-B segment of the present invention is non-crystalline. The bioresorbability and/or crystallinity of the B-C-B segment can be assessed using various methods.

In case the thermal properties of the polyurethane of the present invention is determined by thermal analysis such as differential scanning calorimetry (DSC), the urethane segment does not have a melting peak. This is in strong contrast to the (hard, uniform, and crystallizing) urethane segments in polyurethanes as described in WO99/64491. In a preferred embodiment of the present invention, the B-C-B segment thus essentially does not have a melting peak as determined by DSC.

An alternative method to assess the bioresorbability of the B-C-B segment is by carrying out an in vitro degradation study, wherein a sample of the polyurethane is exposed to degradation medium, typically Sorensen buffer solution with a pH of 7.4 and kept in an incubator at 37° C. according to ISO10993. At certain intervals, the remaining mass of the sample is analyses. In a preferred embodiment of the present invention, less than 10 wt. % of the polyurethane remains after 16 h of exposure to a buffer solution with a pH of 7.4 at 37 ° C.

In preferred embodiments of the present invention, B is at least partially based on a linear or branched $C_4$ to $C_{11}$ alkyl diisocyanate, preferably selected from the group consisting of 1,4-butane diisocyanate (BDI), 1,5-pentane diisocyanate (PDI), 1,6-hexyl diisocyanate (HDI), 1,7-heptyl diisocyanate (HpDI), 1,8-octyl diisocyanate (ODI), 1,9-nonyl diisocyanate (NDI), 1,10-decyl diisocyanate (DDI), methylene bis(4-cyclohexylisocyanate), 2,6-diisocyanatohexanoate and esters thereof (L-lysine diisocyanate, LDI), 5-isocyanate-1-(isocyanomethyl)-1,3,3-trimethylcyclohexane (isophorondiisocyanate, IPDI), and combinations thereof.

In preferred embodiments of the present invention, C is at least partially based on linear or branched $C_4$ to $C_{11}$ alkyl diol, preferably selected from the group consisting of glycol, diethylene glycol, 1,4-butane diol (BDO), 1,5-pentane diol (PDO), 1,6-hexyl diol (HDO), 1,7-heptyl diol (HpDO), 1,8-octyl diol (ODO), 1,9-nonyl diol (NDO), 1,10-decyl diol (DDO), N-methyl diethanolamine (N-MDEA), 2,2-bis(hydroxymethyl)propanoic acid, tartartic acid, polyethylene glycol, polycaprolactone, poly lactide and combinations thereof.

In the embodiment wherein the urethane segment is of a multiform length, C may also be a diol that is a XYX reaction product of diol (X) and diisocyanate (Y), wherein diol (X) is a diol selected from the group consisting of glycol, diethylene glycol, 1,4-butane diol (BDO), 1,5-pentane diol (PDO), 1,6-hexyl diol (HDO), 1,7-heptyl diol (HpDO), 1,8-octyl diol (ODO), 1,9-nonyl diol (NDO), 1,10-decyl diol (DDO), N-methyl diethanolamine (N-MDEA), 2,2-bis(hydroxymethyl)propanoic acid, tartartic acid, polyethylene glycol, polycaprolactone, poly lactide and combinations thereof and diisocyanate (Y) is a diisocyanate selected from the group consisting of 1,4-butane diisocyanate (BDI), 1,5-pentane diisocyanate (PDI), 1,6-hexyl diisocyanate (HDI), 1,7-heptyl diisocyanate (HpDI), 1,8-octyl diisocyanate (ODI), 1,9-nonyl diisocyanate (NDI), 1,10-decyl diisocyanate (DDI), methylene bis(4-cyclohexylisocyanate), 2,6-diisocyanatohexanoate and esters thereof (L-lysine diisocyanate, LDI), 5-isocyanate-1-(isocyanomethyl)-1,3,3- trimethylcyclohexane (isophorondiisocyanate, IPDI) and combinations thereof.

The mechanical properties of the polyurethane can be further improved by allowing C to comprise a small amount (e.g. 0.01 to 10 mol %) of triol. Examples of suitable triols include glycerol, triethanolamine, and the like. The presence of a small amount of triol may result in a (partial) cross-linking of the polyurethane.

At least part of the diol C may be substituted with a $C_1$-$C_{10}$ hydrocarbon, comprising a carboxylic acid, nitrile, isonitrile or protected S, N, P or O, for instance with a propionic acid side group. These groups enable further functionalization of the polyurethane with for instance an activated ester, an acid chloride, an anhydride, an aldehyde, p-nitrophenyl carbonate, an epoxide, an isocyanate, a vinyl sulfone, maleimide, o-pyridyl-disulfide or a thiol. Examples of substituted diols that are suitable are 5-hydroxy-3-(hydroxymethyl)valeric acid, 2,2-bis(hydroxymethyl)propanoic acid, tartaric acid, and the like.

With the number of linear atoms in the back bone of a block is meant the smallest number of atoms that are located in the back bone of a block. For instance, when the backbone comprises a cyclic moiety such as IPDI, the smallest number of atoms between the urethane bonds (i.e. are to be counted. Thus, e.g. in the case of a IPDI-ODO-IPDI block, the number of linear atoms in the backbone of the block is 16 (4+8+4).

The polyol can comprise any diol, triol, tetraol, etc. or a mixture thereof. For instance, the polyol can comprise any of the diols described herein for the diol component C in $(A-B-C-B)_n$. Polyol A may comprise the same or different diol molecules as diol component C does. In preferred embodiments, the polyol has an average molecular weight in the range of 500 to 10000 g/mol.

Preferably, the polyol comprises a prepolymer. Examples of suitable prepolymers include poly(alkene oxides) such as polyethylene glycol (PEG), polyesters such a polycaprolactone (PCL) or polylactic acid) (PLA), or mixtures thereof. Preferably, the prepolymer comprises a polyester.

Prepolymer that may be used in accordance with the present invention are disclosed in WO99/64491. The prepolymer to be used in accordance with the invention will preferably be linear, in particular it will comprise a polyester such as a random copolyester, and comprise reactive end groups. These end groups may be hydroxyl or carboxyl. It is preferred to have a dihydroxy terminated prepolymer, but hydroxy-carboxyl or dicarboxyl terminated prepolymer can also be used. The nature of the endgroups is determined by the type of co-monomers, the amounts thereof, the type of starter (if used), and the reaction conditions of the preparation of the prepolymer.

Suitable monomers for the prepolymer comprising the polyester are the cyclic monomers that can be polymerized under ring-opening polymerization conditions. Examples of cyclic monomers are lactide (L, D, LD, meso), glycolide, ε-caprolactone, δ-valerolactone, trimethylenecarbonate, tetramethylenecarbonate, 1,5-dioxepane-2-one, para-dioxanone, and combinations thereof. In a further preferred embodiment, A is a polyester derived from exclusively lactide and ε-caprolactone, typically with a molecular weight between 1000 and 4000.

In case the prepolymer is at least partially linear, it can be prepared using at least partially a difunctional component (e.g. a diol) as starter, but in case a tri- or higher than three functional components is used, star shaped prepolymers may be obtained.

In a particular embodiment of the present invention, the polyol segment comprises a hydrophilic segment. Examples of prepolymer segments comprising hydrophilic segments are described in WO2004/062704, which is incorporated herein in its entirety. The presence of the hydrophilic segment increases the absorption capacities of the device based on the polyurethane polymer and may also influence the rate of biodegradation. The hydrophilic segment may for instance be derived from polypeptide, poly(vinyl alcohol), poly(vinylpyrrolidone), poly(hydroxymethylmethacrylate) or polyethers. A hydrophilic segment is preferably a polyether, such as poly(ethylene glycol).

In case the polyol segment comprises a hydrophilic segment, said polyol segment preferably comprises polyethylene glycol in a content of 1-80 wt %, more preferably 5-60 wt %, even more preferably 20-50 wt %, most preferably 50 wt %.

In a most preferred embodiment, the polyol segment is a prepolymer segment based on about 25 wt. % lactide, about 25 wt. % ε-caprolactone and about 50 wt. % of polyethylene glycol.

The products of the present invention show a good balance between the properties necessary for use thereof in biomedical applications, such as good modulus, tensile strength and compression modulus. It has been found possible to process these materials into porous implants by salt-leaching and freeze-drying, typically resulting in a material having macropores in the range of 150 μm to 300 μm. The material can also be produced in situ in an extruder, even in combination with generating macropores in situ.

Tissue-Reactive Polymer

The tissue-adhesive properties of the polymer blend originate inter alfa from the tissue-reactive polymer that comprises a tissue-reactive group. The tissue-reactive polymer described herein is therefore also referred to a tissue-adhesive polymer.

With 'tissue-reactive functional group' is meant any chemical group, functionality or moiety that may react with tissue and form a covalent bond. Cells (and thus the tissue that is formed by cells) typically contain protein and carbohydrates on the outer surface that may react in a variety of reactions. The present invention is thus based on the idea that the tissue-reactive polymer reacts with the tissue and a covalent bond is formed.

For instance, amines of proteins may react with activated esters to form amide bonds, a sulfide may react with another sulfide to form a disulfide bond or amines may react with the functional group to form urethane bonds. It may be appreciated that other bonding types, such as Van-der-Waals interactions, hydrogen bonding, ionic interaction and the like, may also play a role in the overall bonding capacity of the tissue-reactive polymer of the present invention. The specific occurrence and strength of each type of bonding generally depends on the type of tissue, the chemical composition of the tissue-reactive polymer and the structure of the device based thereon.

The tissue-reactive functional group is appropriately stable in an aqueous environment, but at the same time sufficiently reactive with respect to the tissue. Although the tissue-reactive functional group may be sensitive to hydrolysis, appropriately stable means that the group remains stable for a period long enough for the tissue-adhesive polymer to react with the tissue. As such, preferred tissue-reactive polymers in accordance with the present invention comprise a tissue-reactive functional group that is an activated ester, an acid chloride, an anhydride, an aldehyde, p-nitrophenyl carbonate, epoxide, an isocyanate, vinyl sulfone, maleimide, o-pyridyl-disulfide, a thiol or combinations thereof. Activated esters, acid chlorides, anhydrides, aldehydes, vinyl sulfone, maleimide and isocyanates are electrophilic groups that may typically react with an amine or another nucleophile of the tissue. Thiol or o-pyridyl-disulfide may form a disulfide bond with the tissue.

Examples of conventional tissue-reactive polymers that are suitable as the tissue-reactive polymer include polymers functionalized with activated esters such as N-hydroxysuccinimide (NHS) esters. It is generally believed that these polymers can react with amine groups of the tissue to form covalent amide bonds between the tissue and the polymers and that this reactivity provides the tissue-adhesive properties. A specific example of a conventional tissue-adhesive polymer is the 4-arm succinimidyl glutarate terminated poly(ethylene oxide) having an average molecular weight $M_n$ of 10.000 (CAS number 154467-38-6, also referred to as 4-arm-PEG10k-SG) as represented by the formula:

(4-arm-PEG10k-SG)

Drawbacks of the 4-arm-PEG10k-SG and similar polymers is that the amide bond formed with the tissue and the presence of the ester bond results in a relatively weak tissue-adhesion, in particular at the long term. In general, it is desired that the adhesive-strength between the polymers and the tissues is large, in particular at the long term (i.e. several days to weeks). Accordingly, it is preferred that the tissue-adhesive polymer that provides an improved adhesive-strength at longer term.

It was surprisingly found that an improved tissue adhesive strength can be obtained with a multi-arm polymer wherein at least two or more arms each comprise a reactive functional group that can form a urethane, a thiourethane or a urea bond with an amine group present in tissue. The reactive functional group is herein accordingly also referred to as the tissue-reactive group.

Functional groups that are capable of forming a urethane can be represented by the formula X—C(O)—LG, wherein X is an oxygen atom 0 and LG represents a leaving group. As such, upon formation with tissue (i.e. animal or bodily tissue), the leaving group LG may leave and the tissue-adhesive polymer is covalently bound to the tissue via the O—C(O)—NH, i.e. urethane, bond. Similarly, functional groups that are capable of forming a urea can be represented by the formula X—C(O)—LG, wherein X is a nitrogen atom N and LG represents a leaving group. As such, upon formation with tissue (i.e. animal or bodily tissue), the leaving group LG may leave and the tissue-adhesive polymer is covalently bound to the tissue via the N—C(O)—NH, i.e. urea, bond. Functional groups that are capable of forming a thiourethane can be represented by the formula X—C(O)—LG, wherein X is an sulfur atom S and LG represents a leaving group. As such, upon formation with tissue (i.e. animal or bodily tissue), the leaving group LG may leave and the tissue-adhesive polymer is covalently bound to the tissue via the S—C(O)—NH, i.e. thiourethane, bond. Accordingly, in a particular embodiment the multi-arm tissue-adhesive polymer is a polymer according to formula I:

(I)

wherein m is an integer of 2 or more, preferably in the range of 2-12, more preferably 4-10, even more preferably 6-8, most preferably in is 8;

LG represents a leaving group;

X is selected from S, NH and O;

$R^1$ represents a polymeric group; and

Y represents a core structure;

such that $R^1$-X—C(O)—LG represents each arm comprising the reactive functional group X—C(O)—LG.

The tissue-adhesive polymer can be based on a variety of polymers or polymeric groups. The invention is not necessarily limited to poly(ethylene glycol) like the most commonly used conventional multi-arm polymers are. However, it was found that good reaction with the tissue (i.e. good adhesion) can in particular be obtained if the tissue-adhesive polymer is based on a hydrophilic polymer. Examples of suitable hydrophilic polymers include hydrophilic polyether, polyester, polycarbonates, polyurethanes, polyetherurethanes, polyurethane urea, poly(vinylpyrrolidone), poly(saccharide), poly(vinyl alcohol), polyoxazoline, or combinations thereof. The presence of a hydrophobic polymeric part is not necessarily excluded, as long as this is not detrimental to the adhesive properties of the tissue-adhesive polymer. For instance, the hydrophobic part can be overruled by a hydrophilic part of the tissue-adhesive polymer such that overall the polymer remains adhesive to tissue.

Particularly preferred polymeric groups include polyether, polyester, polycarbonate such as poly(alkylene glycol) or a poly(lactic acid), poly(caprolactone), polydioxanone, poly(glycolide) or a poly(trimethylene carbonate). Although polyesters such as poly(lactic acid) and poly (caprolactone) show favorable hydrophilic properties, the present of the ester bonds in the polymers, in particular when combined with ethers, results in a shorter adhesion than the polyether and polycarbonate. Accordingly, even more preferably the polymer or polymeric group comprises poly (ethylene glycol) (PEG), polycaprolactone (PCL), polylactic acid) (PLA), for instance poly(L-lactic acid) (PLLA), a co-polymer of PCL and PLA or a poly(trimethylene carbonate) (PTMC), most preferably PEG.

The reactive functional group comprises a leaving group LG that leaves upon the reaction with an amine. As long as the leaving group is not detrimental to the reactivity of the tissue-adhesive polymer with the tissue, the leaving group is not of a major influence to the adhesive strength because it leaves the polymer and the tissue after reaction. The tackiness of the polymer towards the tissue can however be influence with the choice of the leaving group since the leaving group can influence the reaction rate of the polymer towards the tissue. The reaction rate should not be too low such that the adhesion will practically not occur, but it should neither be too high such that the reactive group will be too prone to a reaction with other components than the tissue such as water. In this respect, it was found that preferably the leaving group LG is an alcohol radical comprising an electron-withdrawing group, preferably an alcohol radical wherein the alcohol is selected from the group consisting of perfluoroalkyl alcohol, p-nitro-phenol, 3,4,5-trichlorophenol, pentafluorophenol, 1-benzotriazolyl alcohol, 1-hydroxy-7-azabenzotriazole, 1-hydroxybenzotriazole, and N-hydroxysuccinimide alcohol and derivatives thereof such as N-hydroxymaleimide, N-hydroxyphthalimide, endo-N-hydroxy-5-norbornene-2,3-dicarboximide and a N-hydroxysulfosuccinimide salt, more preferably wherein the alcohol is a N-hydroxysuccinimide alcohol.

The multi-arm nature of the polymer can be attributed to a core (also referred to as initiator) which has multiple reactive groups to which the arms can be connected. The core or initiator can appropriately be selected based on the polymeric part on which the arms are based. For instance, in the preferred embodiments wherein the polymeric group comprises polylactic acid), glycolide, caprolacton, poly(ethylene glycol) and/or a poly(trimethylene carbonate), the core can be based on a polyol such as glycerol (GL), pentaerythritol (P), hexaglycerol (HG), tripentaerytritol (TP), trimethylolpropane (TMP) and dipentaerythritol (DP). As such, in a preferred embodiment, Y of formula I is based on a polyol comprising in hydroxyl groups, preferably wherein Y is based on a polyol of structures II, III or IV as depicted below.

II

III

IV wherein each $R^2$ is individually H or each $R^3$ is individually H or each $R^4$ is H or

The $R^2$, $R^3$ and $R^4$ can be selected based on the amount of desired hydroxyl groups. For instance, hexaglycerol (HG) can be represented as pentaerythritol as formula III, wherein each $R^2$ of formula III is In a particular embodiment, the core is the initiator for the preparation of a multi-arm PEG, which is then used as a subsequent initiator in a polymerization reaction with lactide, trimethylenecarbonate, glycolide or caprolacton to form a multiarm block copolymer comprising a multi-arm PEG segment extended with one or more of these monomers. Another possibility is to initiate said polymerization reaction with lactide, trimethylenecarbonate, glycolide or caprolacton directly from the core, thus without the presence of PEG.

It is noted that Y may comprise ($R^1$—X—C(O)—LG) as the sole substituent, but it may also comprise further groups (e.g. non-tissue-reactive groups) such as for instance $R^1$—X—H. Generally, it is preferred that all arms comprise the tissue-reactive group, but it may be that, e.g. due to limitation in the method for preparation (vide infra), not all arms are substituted with the tissue-reactive group. The degree of arms that comprise the tissue-reactive group is herein expressed as the substitution degree. The substitution degree can be determined by 1H-NMR in combination with the following formula $$\text{substitution degree } (\%) = \frac{A}{Q \times R} \times \frac{Z \times M_n}{B \times M_w} \times 100\% \qquad \text{(IV)}$$

wherein:
A is the area of the peak or peaks corresponding to all the protons of the leaving group;
Q is the number of protons in leaving group;
R is the total number of arms of the tissue-adhesive polymer;
B is the area of the peak or peaks corresponding to all the protons of polymer arms;
Z is the number of protons in the monomer on which the polymeric group is based;
$M_w$ is the molecular weight of monomer on which the polymeric group is based;
$M_n$ is the number-average molecular weight of the tissue-adhesive polymer without the reactive functional groups.

Good adhesive strengths were obtained when the substitution degree is more than 60%, preferably more than 80% as determined by $^1$H-NMR.

It was further surprisingly found that the tissue-adhesive properties of the polymer increase with the number of arms and as well as with the number-average molecular weight ($M_n$) of the polymer. In addition, better adhesion is obtained with an improved length of each arm that comprises the functional reactive group. It is thus not necessarily the case that the total amount of functional reactive groups determines mainly the adhesive strength. In certain embodiments, the adhesive strength can be mainly correlated to the amount of arms comprising the functional reactive groups in combination with the molecular weight. Since from a toxicological point of view, a low amount of function reactive groups is desired, it may be preferred that the amount of functional reactive groups is less than 5%, more preferably less than 4%, most preferably less than 3%, based on the total weight of the tissue-adhesive polymer. These amounts are particular applicable on NHS as the functional reactive group.

The length of the arms can be expressed with their molecular weight. Accordingly, on average, the number-average molecular weight ($M_n$) of each arm is preferably in the range of 500 Da to 50 kDa, more preferably 1-25 kDa, most preferably 2 to 10 kDa. In addition, number-average molecular total weight of the multi-arm tissue-adhesive polymer is preferably in the range of 5 to 100 kDa, more preferably in the range of 10-80 kDa, most preferably in the range of 20-60 kDa. For instance, very good results were obtained with an 8-armed (PEG) having a number-average molecular weight of 40.000 g/mol (i.e. 40 kDa), of which each arm is thus about 5 kDa. The number-average molecular weight can be determined by known analytical techniques such as size exclusion chromatography (SEC) and/or matrix assisted laser desorption ionization time of flight mass spectrometry (MALDI-TOF-MS).

The polymer of the present invention is particularly suitable for application in medical devices such as medical foams and medical sheets. It may further suitably be applied on tissue as a spray to form a tissue cover or sealing in situ.

In a preferred embodiment of the present invention, the tissue-adhesive layer further comprises a buffering agent, preferably blended with the carrier polyurethane and the tissue-adhesive polymer. A buffering agent capable of maintaining a pH of more than 7 is preferred. More preferably, the buffering agent is capable of maintaining the pH in the range of 8 to 10. It was surprisingly found that the presence of the buffering agent improved the tissue-adhesive properties of the tissue-adhesive device, in particular at the long term (i.e. several days and weeks). Without wishing to be bound by theory, the inventors believe that the buffering agent provides locally a favorable (preferably elevated) pH-value under which the rate of the reaction of the tissue with the tissue-reactive polymer is higher. Typically, the buffering agent may be present in an amount of at least 0.1 mg/cm$^3$, preferably in an amount in the range of 0.5 to 15 mg/cm$^3$, more preferably in a range of 2 to 10 mg/cm$^3$, even more preferably in a range of 3 to 5 mg/cm$^3$ such as about 4% based on the volume of the tissue-adhesive layer. This range is particularly preferred for Na$_2$HPO$_4$. For other buffering agents, the amount can be different.

The buffering agent is preferably not detrimental to the degradation properties of the polymer blend. In addition, the buffering agent is preferably biocompatible. Accordingly, the buffering agent is preferably selected from the group consisting of phosphates (e.g. Na$_2$HPO$_4$), carbonates, borates, acetates, citrates, Good's buffers (preferably those applicable in a pH range of more than 7, more preferably more than 8) such as bicine and the like.

In a particular embodiment, additionally to the carrier polyurethane and the tissue-reactive polymer, a filler polymer may be present. The filler polymer is typically based on polyethylene glycol that is not functionalized with the tissue-reactive functional group. The function of the filler polymer is to provide stiffness to the carrier polyurethane.

In a particularly preferred embodiment, the device essentially consists of the tissue-adhesive urethane and the tissue-adhesive polymer. In the context of the present invention, essentially consisting of means that at least 90%, preferably more than 95% of the device consists of the tissue-adhesive urethane and the tissue-adhesive polymer, based on the total weight of the device. Other components such as drugs (e.g. hemostatic, anti-inflammatory agents and the like), may also be present in the device, as long as these components do not undesirably interfere with the adhesive properties of the device.

The device may have a foam structure, a sheet structure, a gel-like structure or combinations thereof. Particular good results have been obtained with the device wherein the tissue-adhesive layer has a foam structure, which is therefore preferred. The porosity of the foamed tissue-adhesive layer is preferably in the range of about 60-99.9%, preferably 70-98%, more preferably 80-98%. The appropriate porosity can be obtained during the preparation of the device, for instance by providing a certain concentration of the polymers in a solution and subsequently removing the solvent by freeze drying to obtain a porous foam. A higher concentration of the polymers results in a lower porosity and vice versa.

The tissue-adhesive layer in accordance with the present invention typically has a total density in the range of about 40 to 250 mg/cm$^3$. This total density can further be specified by regarding the density of the various components in the tissue-adhesive layer. Preferably, the density of the polyurethane carrier in the tissue adhesive layer is in between 20-110 mg/cm$^3$, the density of the tissue-adhesive polymer is preferably between 10-200 mg/cm$^3$ and the density of the buffering agent, is present, is preferably between 0.1 and 25 mg/cm$^3$.

The inventors have surprisingly found that the total density of the tissue-adhesive layer influences the adherence of the device on different tissues. For instance, on smooth tissues such as collagen and liver capsule, a device having a higher total density, e.g. a total density in the range of about 50 to about 80 mg/cm$^3$ provides good adherence, while on rougher tissues such as liver tissue that is exposed upon resection, such a device can provide poorer adherence than a similar device having a higher porosity, e.g. a total density of 80 mg/cm$^3$ or higher, such as in the range of 80 to 130 mg/cm$^3$ Without wishing to be bound by theory, the inventors believe that a lower total density results in a less flexible device and a poorer conformation of the shape to the contours of the tissue. A higher total density results in more flexibility and thus in a better conformation of the shape to such contours and a better adherence.

The tissue-adhesive device may have a multilayered structure comprising at least two layers. In a preferred embodiment, the tissue-adhesive layer is adjacent to a further layer, e.g. a sheet layer. A particularly suitable arrangement is a foamed tissue-adhesive layer in combination with the adjacently placed sheet layer. The sheet layer may for instance comprise a biodegradable polyester or a polyurethane. Preferably, the sheet layer comprises a polyurethane as described herein-above, more preferably the sheet layer comprises the same carrier polyurethane as the tissue-adhesive polymer. This improves the compatibility between the sheet layer and the (foamed) tissue-adhesive layer such that the layers do not separate after application.

The concentration of the tissue-reactive polymer may be constant in the tissue-adhesive layer or may gradually increase in the direction perpendicular to the plane of the device that is to be applied to the tissue. In the embodiments wherein the concentration gradually increases, the required amount of tissue-reactive polymer may be limited, which may be beneficial for an efficient use of the tissue-adhesive polyurethane.

Figure 1:
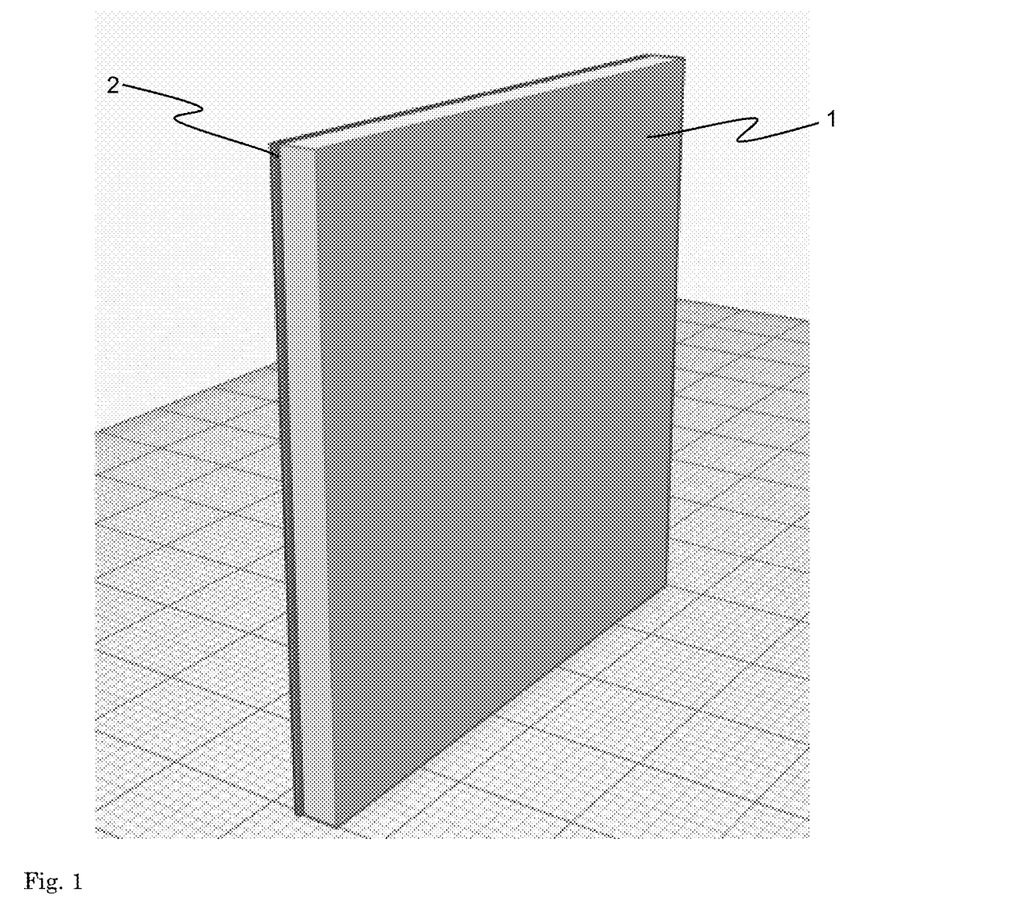
FIG. 1 depicts a tissue-adhesive device as disclosed herein.

In a preferred embodiment of the device, as illustrated in FIG. 1, the device comprises a foamed tissue-adhesive layer (1) which is optionally at least partially covered by sheet layer (2). It was found that the sheet layer can provide additional resistance towards leakage and can provide mechanical strength to limit burst of the device due to pressure. It is preferred that the sheet layer is colored differently than the foam layer such that when in use, the tissue-adhesive (foam) layer can more easily be distinguished form the sheet layer.

The tissue-adhesive device and/or the blend in accordance with the present invention may be for use in a method of surgery, in particular in a method of sealing the ventral cavity (including the abdominal, thoracic and pelvic cavities) like liver, lung, pancreas, spleen, bladder, kidney and/or intestine tissues. The breakdown of the device typically occurs after 7 days, preferably after 14 days even upon exposure to bile and other bodily fluids such as air, intestinal fluids, stomach juice and the like is also preferred such that for instance anastomotic and esophageal perforation leakage may also be treated.

As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features.

For the purpose of clarity and a concise description features are described herein as part of the same or separate embodiments, however, it will be appreciated that the scope of the invention may include embodiments having combinations of all or some of the features described.

The invention can be illustrated by the following non-limiting examples.

EXAMPLE 1

Synthesis of Carrier Polyurethanes

A polyol (50 g, 0.025 mol, 2000 g/mol) was synthesized from DL-lactide and $\epsilon$-caprolactone using butanediol as an initiator and stannous octoate as a catalyst at a temperature of 140° C. for 14-17 days under nitrogen atmosphere. The polyol was subsequently reacted with 3.5 g (0.05 mol, 2 eq.) of butanediisocyanate (BDI). After complete conversion (within 1 h), the concentration isocyanates ([NCO]) was determined using FT-IR. This [NCO] is used to determine the amount of chain extender diol component (1,6-hexanediol, HDO) which needs to be added to obtain the 3-block polyurethane. The following equation was used:

$$\text{Mass } HDO(\text{mg}) = \frac{[NCO] \times (m_{polymer} + m_{BDI}) \times M_{HDO}}{2} \times 0.98$$

1,4-dioxane was added as the solvent (ratio 1:1) and the reaction mixture was heated to 90° C. The reaction mixture became viscous over time and the [NCO] was monitored during the reaction using FT-IR. After complete conversion of the available NCO groups, the reaction mixture was diluted with 1,4-dioxane.

A series of polyurethanes was prepared in a method similar as described above. The same polyol was used, but different diisocyanate moieties and/or diol components were used. The obtained polyurethanes are provided in Table 1.

TABLE 1

| Polyurethane | B-C-B segment[1] | Mw (g/mol) | Mn (g/mol) |
|---|---|---|---|
| PU1 | BDI-BDO-BDI | 66200 | 49900 |
| PU2 | BDI-BDO-BDI-BDO-BDI | 56400 | 35300 |
| PU3 | HDI-HDO-HDI | n.d. | n.d. |
| PU4 | BDI-HDO-BDI | 61400 | 44200 |
| PU5 | BDI-ODO-BDI | 57700 | 37400 |
| PU6 | HDI-BDO-HDI | 63100 | 41000 |
| PU7 | HDI-ODO-HDI | 48800 | 31300 |

[1]in A-B-C-B polymer wherein A copolymer of DL-lactide and $\epsilon$-caprolactone with BDO as an initiator;

EXAMPLE 2

Synthesis of Tissue-Adhesive Polymers

The synthesis of a succinimidyl carbonate terminated 8-arm PEG having a molecular weight of 40 kDa (8-arm-PEG40k-SC) was carried out in accordance with the following scheme and the procedure below.

Disuccinimidylcarbonate (0.03 mmol, 256.17 g/mol, 3 equivalents, 7.69 g) was added while stirring to commercially available 8-Arm-PEG40k-OH (1.25 μmol, 1 equivalent, 50 g) in dichloromethane (100 mL) and acetonitrile (200 mL). Pyridine (5 mL) was added. The reaction mixture was stirred for 4 h and the solvent was removed in vacuo. The residue was dissolved in 450 mL of ethyl acetate while heating (45° C.). An amount of 450 mL of tert-butylmethyl ether (TBME) was added to the mixture and the result was subsequently cooled in a freezer. A white solid (43 g, 83% yield) was formed which was purified by crystallization.

Six different batches gave a substitution degree in the range of 91-97%. Higher substitution degrees may be obtained by increasing the reaction time and/or the equivalents of the succinimidyl carbonate.

This procedure was repeated with different starting polymer compounds to obtain the corresponding multi-arm tissue-adhesive polymers as provided in Table 2. The nomenclature in Table is constructed follows [number of arms]-[polymeric group][number-average molecular weight][(core)]-[reactive group]. Thus 8-arm-PEG40k(HG)-SC corresponds to succinimidyl carbonate (SC) terminated 8-arm PEG having a molecular weight of 40 kDa which is based on a hexaglycerol core.

TABLE 2

| tissue-adhesive polymer (TAP) | multi-arm tissue-adhesive polymer |
|---|---|
| TAP1 | 8-arm-PEG40k(HG)-SC |
| TAP2 | 4-arm-PEG10k(HG)-SC |
| TAP3 | 4-arm-PEG20k(HG)-SC |
| TAP4 | 6-arm-PEG15k(DP)-SC |
| TAP5 | 8-arm-PEG20k(HG)-SC |
| TAP6 | 8-arm-PEG40k(TP)-SC |
| TAP7 | 8-armPCL40k(HG)-SC |
| TAP8 | 8-armPLA40k(HG)-SC |
| TAP9 | 8-armPCL/PLLA40k(HG)-SC |

EXAMPLE 3

Preparation of Device

A two-layered device comprising the tissue-adhesive layer and the sheet layer in accordance with the present invention was prepared as follows.

The sheet layer was prepared as follows.

A dye solution of 1 mg/mL D&C Green dye in chloroform (50 mL) in a Duran laboratory bottle of 100 mL was stirred for a period of 0.5 h.

A polyurethane solution was prepared by adding the required amount of chloroform (example for 12 devices; dissolve 13.12 gram of carrier polyurethane PU5 into 162.85 ml chloroform), and stirring the mixture for a period of 4 h.

Next, 6.79 mL of the dye solution was added to the 162.85 ml polyurethane solution and part of the mixture was added into a mold of 7×7 The mold was covered and left for 16 h. Next, the cover was removed from the mold and the sheets were left to dry for an additional 6 h, followed by placing the mold in the vacuum oven for 16 h to ensure the complete removal of the solvent.

The tissue-adhesive layer was prepared on the sheet layer as follows.

The mold containing the (green)polyurethane sheets was taken from the vacuum oven and placed in a freezer at a temperature of −28° C. for a period of 4 hours.

A solution of the carrier polyurethane PU5 (4.84 g in 152 mL of 1,4-Dioxane) was prepared and stirred until the carrier polyurethane was entirely dissolved in 1,4-Dioxane (approximately 1 h). When the carrier polyurethane was dissolved, 190 mg of sodium phosphate dibasic ($Na_2HPO_4$) as the buffering agent was added. The mixture was stirred for 1h. An amount of 1.9 g TAP1 as the tissue-adhesive polymer was added to the mixture.

Next, about 12 ml of the prepared solution of the carrier polyurethane was poured on top of the sheet layer inside the mold.

The result was freeze dried to remove the solvents and obtain the two-layered device.

Several further two-layered devices comprising the tissue-adhesive layer and the sheet layer were similarly made with varying amounts of the carrier polyurethane (mg/cm$^3$) and buffering agent (mg/cm$^3$) while maintaining the concentration of the tissue-adhesive polymer constant at 31 mg/cm$^3$, as indicated in Table 3.

TABLE 3

| Device Nr. | Composition | PU5 (mg/cm$^3$) | TAP1 (mg/cm$^3$) | $Na_2HPO_4$ (mg/cm$^3$) |
|---|---|---|---|---|
| 1 | DP2.5 3% PG25 | 40 | 31 | 3 |
| 2 | DP2.5 4% PG25 | 54 | 31 | 3 |
| 3 | DP2.5 5% PG25 | 68 | 31 | 3 |
| 4 | DP2.5 7% PG25 | 97 | 31 | 3 |
| 5 | DP5.0 3% PG25 | 40 | 31 | 6 |
| 6 | DP5.0 5% PG25 | 68 | 31 | 6 |

EXAMPLE 4

Tensile Strength (N) and Burst Strengths (mbar) of Devices on Collagen

The tensile strengths and burst strengths (mbar) of the device of Example 3 on collagen (PCC) were determined as follows.

Dry collagen sausage casing (#190; Nippi Co., Japan) was submerged in a solution of 1 mL ethylenediaminetetraacetic acid (EDTA) in phosphate-buffered saline, pH 7.4, and heated at 80° C. for 20 min. The sausage casing was then extensively washed with distilled water and stored submerged in 0.1M 4-(2-Hydroxyethyl)piperazine-1-ethanesulfonic acid (HEPES), pH 8.0, until use. Prior usage, the sausage casing must be rinsed with demineralized water to remove the buffer salts.

For the tensile strength determination, a 20×50 mm rectangular piece of collagen were cut with a surgical blade. Square test articles of the device (sized 20×20 mm) were cut with a surgical blade. The 20×50 mm rectangular piece of collagen was cut exactly in the middle and wetted with demineralized water. A 20×20 mm test article was placed over the cut and pressed for 10 seconds, subsequently 1 kg of pressure was applied for 2 minutes. Paper clamps with additional sanding paper for grip were used to place the collagen including the test article in the clamps of the tensile tester. The tensile strength was determined with a constant cross-head speed of 10 mm $min^{-1}$ and the load extension diagram was recorded. A graph was generated (load vs extension) and the load at yield (zero slope) is determined as the adhesion strength of the test article.

The measurement was performed at both 0 days as 7 days. For the 7 day time period, the rectangular pieces of collagen containing the test article is placed in Sorensen buffer solution and placed in an incubation oven which was set to a temperature of 37° C. After 7 days, the tensile strength is determined according to the method described above.

For burst pressure testing, a 30 mm circle was punched in the collagen. At the time of use, a 4 mm biopsy punch was made in the centre of the circle. A Teflon ring was placed on the substrate to centre the defect. A 20 mm circular test sample was placed on the defect (pre-wetted with demineralized water) and a weight of 1 kg was place on top of the device for a period of 2 minutes.

The burst pressure setup has a main unit that comprises a pressure vessel connected to a flow sensor and pressure sensor. The flow sensor feeds in to a test location at which a sample can be placed. By regulating the flow sensor, the pressure in the test location can be controlled/build up, thereby making it possible to evaluate what the performance of the sample is in terms of pressure. This pressure was recorded by the aforementioned pressure sensor.

The collagen with the test article was placed onto the fixture base. An O-ring (22 mm ID) was placed on top of the collagen containing the test article and secured by closing with 4 knobs. A water flow rate of 1 mL/min (60 g/h) was applied. During the determination, the maximum pressure was recorded and reported in mbar. The measurement was performed at both 0 days as 7 days. For the 7-day time period, the circular pieces of collagen containing the test article was placed in Sorensen buffer solution and placed in an incubation oven which was set to a temperature of 37° C. After 7 days, the burst pressure was measured according to the method described above.

Figure 2:
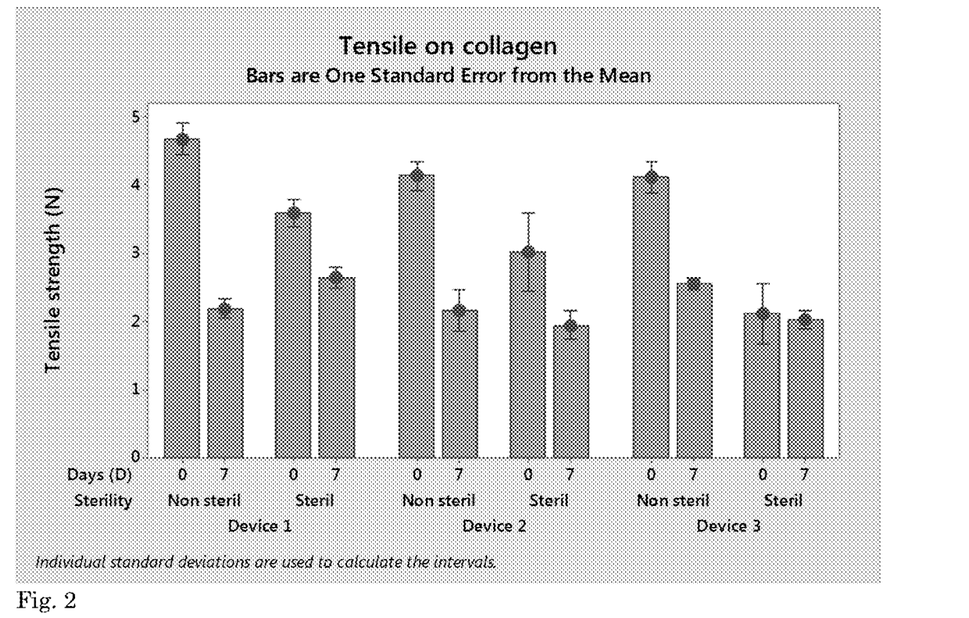
FIG. 2 graphically depicts device tensile strength as disclosed herein.
Figure 3:
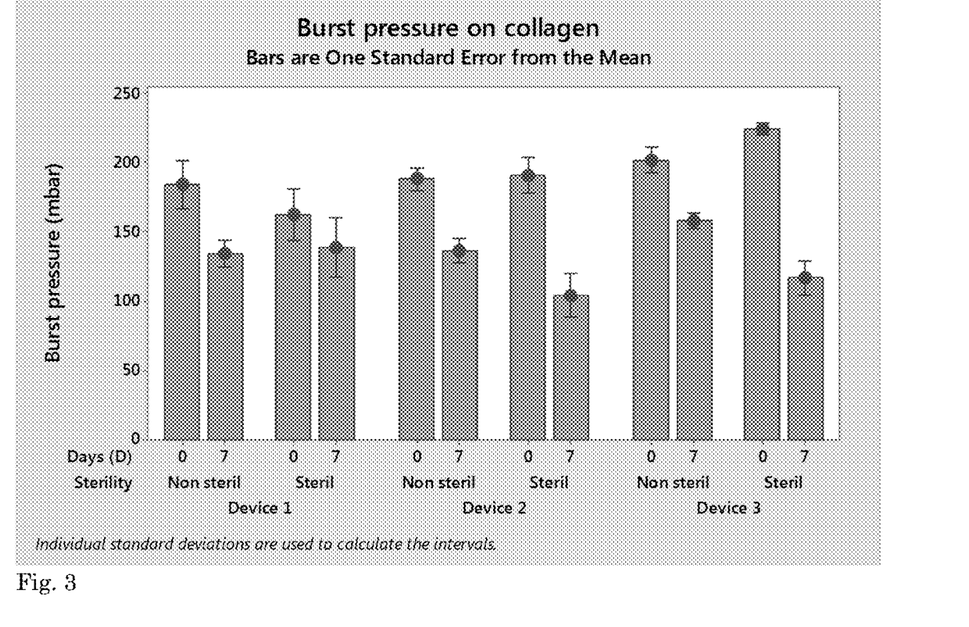
FIG. 3 graphically depicts device burst pressure as disclosed herein.

The results are illustrated in FIGS. 2 and 3.

The figures show that on non-soft tissues like collagen, the carrier polymer concentration does not have an effect on the long-term adherence in terms of tensile strength and burst strengths. It also shows the effect of a higher molecular weight on the long-term adherence.

EXAMPLE 5

Adherence on Liver Capsule (N)

Figure 4:
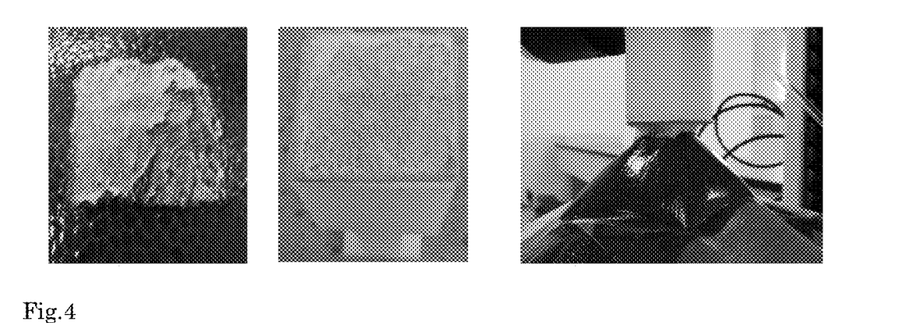
FIG. 4 illustrates adherences of the devices disclosed herein on liver capsule having a smooth surface.

The adherences (N) of the devices of Example 3 on liver capsule having a smooth surface were determined as follows and as illustrated in FIG. 4.

Porcine liver for adherence testing was placed on a petridish. The thickness of the liver substrate varied and towels were used to level the substrate. Test articles of the devices were cut in pieces of 20×20 mm and attached to a piston using 2-sided tape. The surface of the liver was pre-wetted with saline. The test article was pressed on the liver surface using an Instron tensile tester with a ramp of 20 mm/min until a force of 10 N was reached. After 2 min, the test article was removed from the liver surface with 20 mm/min and the force required was measured. The maximum load is reported as being the adherence (N).

Figure 5:
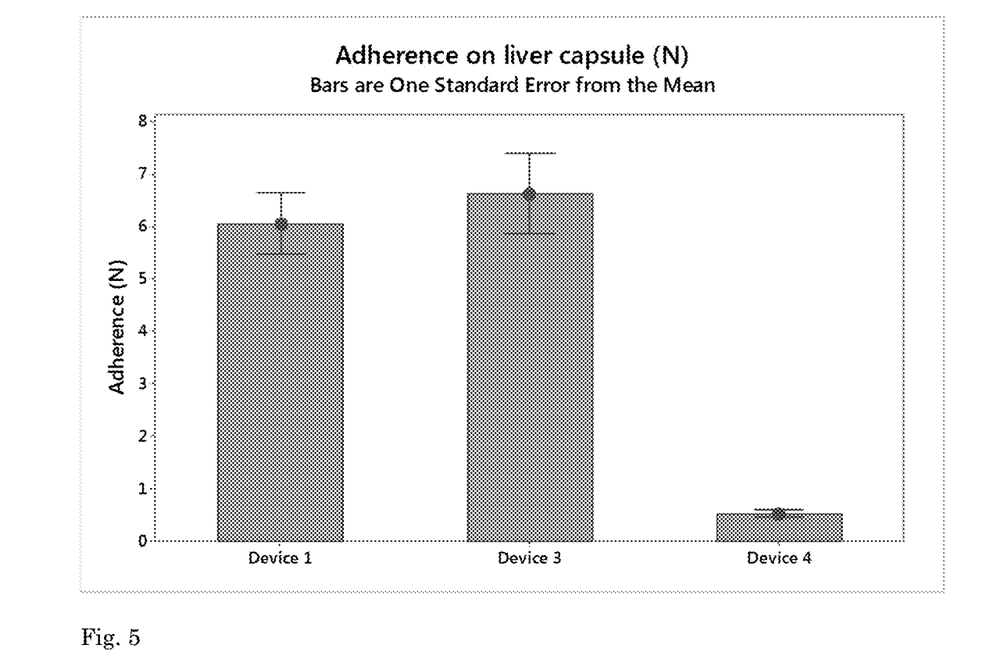
FIG. 5 graphically depicts device adherence on liver capsule as disclosed herein.

The results are illustrated in FIG. 5 that shows that the density of the foam (concentration polymer) layer determines the adherence on liver capsule tissue. The strongest adherence is observed for device nr. 3.

EXAMPLE 6

Adherence on Liver Resected Area (N)

The adherences (N) of the devices of Example 1 on liver resected area having a rougher surface than the liver capsule were determined as described in Example 5 and illustrated in FIG. 4.

Figure 6:
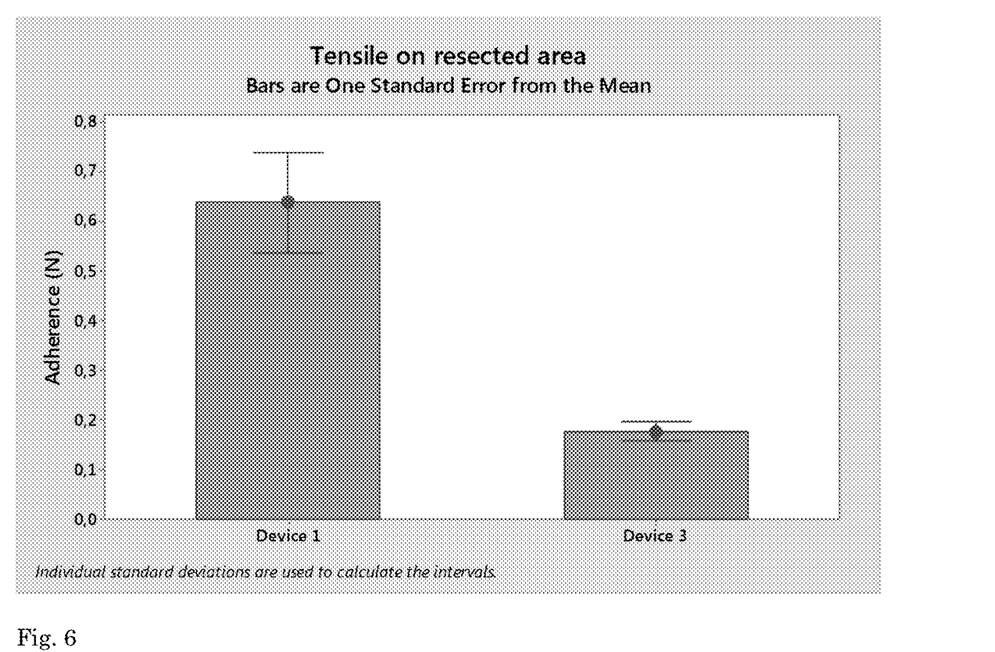
FIG. 6 graphically depicts adherences of the devices disclosed herein on liver resected area having a rougher surface than liver capsule.

The results are illustrated in FIG. 6 that shows that the density of the foam (concentration polymer) layer determines the adherence on liver capsule tissue. The strongest adherence is observed for device nr. 1.

EXAMPLE 7

Comparison with Conventional Devices: Liver Tissue Adhesion

The adherences (N) on liver capsule of the devices of Example 3 and of commercially available devices Tachosil™, Hemopatch™ and Veriset™ were tested as described in Example 5.

Figure 7:
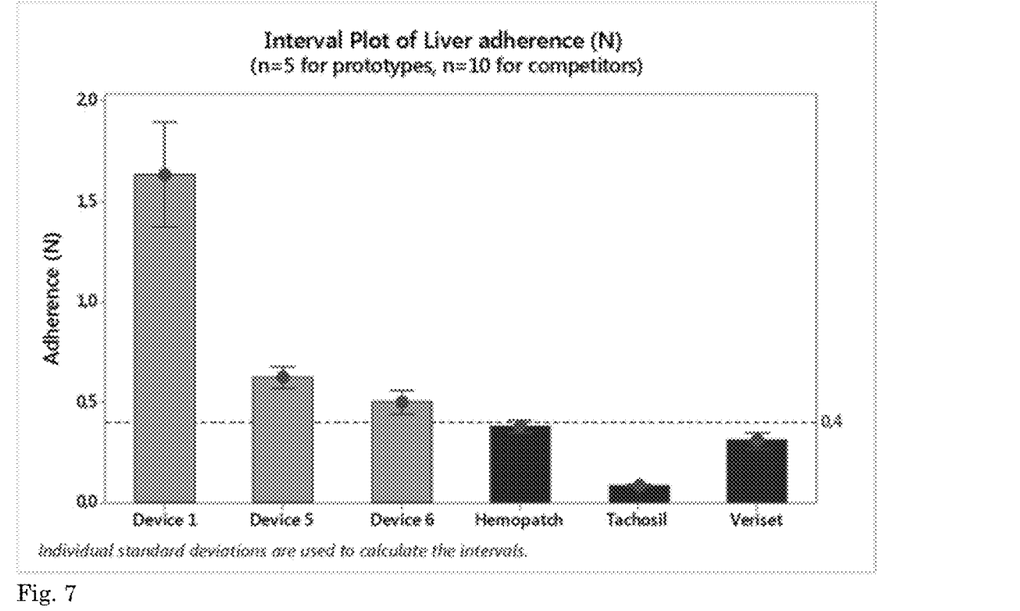
FIG. 7 graphically depicts the interval plot of liver adherence of the devices disclosed herein.

The results are provided in FIG. 7 and show significantly better adherence of the device in accordance with the present invention.

EXAMPLE 8

Additional Comparison with Conventional Devices: In Vitro Tensile Strength Test

The commercially available devices Hemopatch™ and Veriset™ were also compared with Device nr. 1 in the in vitro tensile strength measurements on the collagen-based substrate as described in Example 4. The results are shown in Table 4 for the 0-day period and in Table 5 for the 7-day period.

TABLE 4

Results of tensile strength determination on collagen tissue

| Tissue sealant | N | Mean tensile strength (N) | Standard deviation |
|---|---|---|---|
| Hemopatch ™ | 10 | 0 | 0 |
| Veriset ™ | 13 | 0.5 | 0.6 |
| Device nr. 1 | 10 | 3.5 | 0.6 |

Out of the 3 sealants, the Device nr. 1 had the highest mean tensile strength (3.5±0.6 N), followed by Veriset™ (0.5±0.6 N). Surprisingly, Hemopatch™ did not show any adherence on collagen. The adherence of Device nr. 1 was found to be significantly higher (P<0.05) than the other sealants.

TABLE 5

Results of tensile strength determination on collagen tissue after 7 days in buffer solution

| Tissue sealant | N | Mean tensile strength (N) | Standard deviation |
|---|---|---|---|
| Hemopatch ™ | 10 | 0 | — |
| Veriset ™ | 10 | 0 | — |
| Device nr. 1 | 7 | 2.1 | 0.3 |

In vitro tensile strength measurements on the collagen-based substrate after 7 days in Sorensen buffer solution demonstrates the strongest adherence when using Device nr. 1. Out of the 3 sealants, Device nr. 1 had the highest mean tensile strength (2.1±0.3 N). Surprisingly, in this case Veriset™ also showed no adherence on collagen. The adherence of Device nr. 1 was found to be significantly higher (P<0.05) than the other sealants.

EXAMPLE 8

Additional Comparison with Conventional Devices: In Vitro Burst Pressure Test

The commercially available devices Hemopatch™ and Veriset™ were also compared with Device nr. 1 in the in vitro burst pressure measurements on the collagen-based substrate as described in Example 4. The results are shown in Table 6 for the 0-day period and in Table 7 for the 7-day period.

TABLE 6

Results of burst pressure determination on collagen tissue

| Tissue sealant | N | Mean Burst pressure(mbar) | Standard deviation |
|---|---|---|---|
| Hemopatch ™ | 10 | 0 | — |
| Veriset ™ | 13 | 88.2 | 77.7 |
| Device nr. 1 | 10 | 138.6 | 18.8 |

In vitro burst pressure measurements on collagen tissue demonstrates the highest acute burst pressure when using Device nr. 1. Out of the 3 sealants, Device nr. 1 had the highest burst pressure (138.6±18.8 mbar), followed by Veriset™ (88.2±77.7 N). Again Hemopatch™ did not show any adherence on collagen. The adherence of Device nr. 1 was found to be significantly higher (P<0.05) than the other sealants.

TABLE 7

Results of burst pressure determination on collagen tissue after 7 days in buffer solution

| Tissue sealant | N | Mean Burst pressure(N) | Standard deviation |
|---|---|---|---|
| Hemopatch ™ | 10 | 0 | 0 |
| Veriset ™ | 10 | 0 | 0 |
| Device nr. 1 | 10 | 110.7 | 25.7 |

EXAMPLE 10

Resistance to Bile Fluid

In order to investigate the resistance of the various commercially available devices' materials and the materials of the device according the present invention to bile fluids, the following experiment was carried out. The materials were incubated at a temperature of 37° C. in an excess porcine bile fluid (20 mL) freshly obtained from a local slaughter house. The bile fluid was replaced every 48 h. The materials were removed from the incubation medium after predetermined periods (0 h, 24 h, 96 h and 168 h) and were washed with demineralized water (3×5 mL) on a pre-weighed filter paper using a Buchner funnel. The materials including the filter paper were frozen and subsequently freeze-dried overnight to remove the moisture in the samples. The remaining mass was of the materials was determined.

Figure 8:
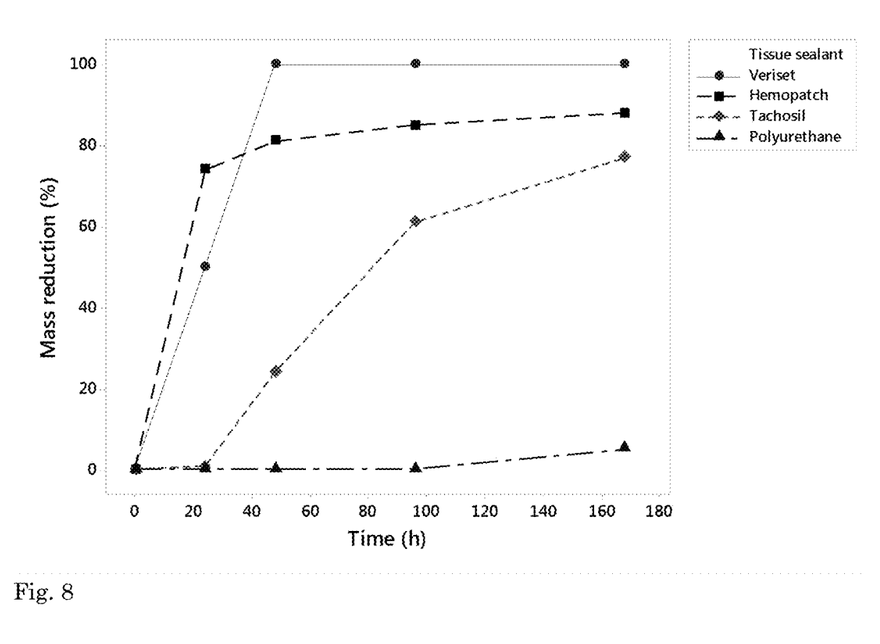
FIG. 8 graphically depicts the remaining mass vs the incubation time of various tissue sealants in bovine bile fluids as disclosed herein.

FIG. 8 shows the remaining mass vs the incubation time of various tissue sealants in bovine bile fluids. The graph clearly shows that the Device nr. 1 (indicated in FIG. 8 as 'Polyurethane') sealant material is the only one that is resistant against bile fluid. Veriset™ dissolves entirely in bile fluid within 48 h. Hemopatch™ shows almost 80% mass reduction within 24 h, followed by Tachosil which shows a mass reduction of almost 80% after 168 h (1 week).

The in vitro studies in Examples 8-10 show that the commercially available products Hemopatch™, Veriset™ and Tachosil™ fail to prevent the leakage of fluids for a prolonged period of time. A major drawback of these commercially available products is that they are not resistant to bile fluids. For example, based on these in vitro experiments, it can be concluded that Veriset™ provides acute adherence on liver and collagen tissue, but it released from the tissue within 24 hours after application as shown with long term tensile and burst pressure testing. These products are therefore not suitable for sealing tissue for a longer period of time and may therefore only have very limited or no effect on reducing complication caused by postoperative bile leakage and re-bleedings.

The invention claimed is:

1. Biodegradable tissue-adhesive device for sealing tissue, said device comprising a tissue-adhesive layer which comprises a blend of a tissue-reactive polymer and a biodegradable carrier polyurethane according to formula A-B-$C_n$, wherein A denotes a polyol, B denotes a diisocyanate moiety, C denotes a diol component and n denotes a number of recurring units, and wherein segment B-C-B is bioresorbable.

2. The biodegradable tissue-adhesive device according to claim 1, wherein the B-C-B segment has a multiform block length.

3. The biodegradable tissue-adhesive device according to claim 1, wherein each diisocyanate unit includes more than 12 carbon atoms.

4. The biodegradable tissue-adhesive device according to claim 1, wherein the tissue-reactive polymer comprises a multi-arm tissue-reactive polymer comprising at least two or more arms each comprising a reactive functional group that can form a urethane or urea bond with amine groups present in tissue.

5. The biodegradable tissue-adhesive device according to claim 1, wherein the tissue-reactive polymer is of formula I (I)

wherein m is an integer of 2 or more;

LG represents a leaving group;
X is selected from S, NH and O;
$R^1$ represents a polymeric group; and
Y represents a core structure.

6. The biodegradable tissue-adhesive device according to claim 5, wherein the polymeric group is selected from the group consisting of polyether, polyester, polycarbonate, polyurethane, polyetherurethane, polyurethane urea, poly(vinylpyrrolidone), poly(saccharide), poly(vinyl alcohol), and polyoxazoline, and combinations thereof.

7. The biodegradable tissue-adhesive device according to claim 5, wherein the leaving group is an alcohol radical comprising an electron-withdrawing group.

8. The biodegradable tissue-adhesive device according to claim 5, wherein the core structure Y is based on a polyol comprising m hydroxyl groups.

9. The biodegradable tissue-adhesive device according to claim 5, wherein m is an integer in the range of 2-12.

10. The biodegradable tissue-adhesive device according to claim 5, wherein m is an integer in the range of 6-8.

11. The biodegradable tissue-adhesive device according to claim 5, wherein the polymeric group is a poly(alkylene glycol), a poly(lactic acid), poly(caprolactone), polydioxanone, poly(glycolide), or a poly(trimethylene carbonate) or combination thereof.

12. The biodegradable tissue-adhesive device according claim 5, wherein the leaving group is an alcohol radical selected from the group consisting of perfluoroalkyl alcohol, p-nitro-phenol, 3,4,5-trichlorophenol, pentafluorophenol, 1-benzotriazolyl alcohol, 1-hydroxy-7-azabenzotriazole, 1-hydroxybenzotriazole, and N-hydroxysuccinimide alcohol and derivatives thereof.

13. The biodegradable tissue-adhesive device according to claim 1, wherein the tissue-adhesive layer comprises a foam structure.

14. The biodegradable tissue-adhesive device according to claim 1, wherein the device further comprises a sealing layer that comprises a sheet structure.

15. The biodegradable tissue-adhesive device according to claim 14, wherein the sheet layer comprises a coloring agent.

16. The biodegradable tissue-adhesive device according to claim 14, wherein the sealing layer comprises a biodegradable carrier polyurethane according to the formula of $A\text{-}B\text{-}C\text{-}B_n$, wherein A denotes a polyol, B denotes a diisocyanate moiety, C denotes a diol component and n denotes a number of recurring units, and wherein segment B-C-B is bioresorbable.

17. The biodegradable tissue-adhesive device according to claim 1, wherein the tissue-adhesive layer further comprises a buffering agent.

18. The biodegradable tissue-adhesive device for sealing tissue according to claim 1, wherein the weight ratio of the tissue-reactive polymer to the biodegradable carrier polyurethane in the tissue-adhesive layer is in the range of 5:1 to 1:10.

19. Biodegradable tissue-adhesive device for sealing tissue according to claim 1 having an adhesive strength on liver tissue of at least 0.4 N as determined by a method a described in Example 5.

20. A method of sealing tissue comprising applying a polymer composition comprising a blend of the tissue-reactive polymer and the biodegradable carrier polyurethane in accordance with claim 1 to tissue in a manner to seal a ventral cavity.

* * * * *